(12) United States Patent
Beck

(10) Patent No.: US 7,202,541 B2
(45) Date of Patent: Apr. 10, 2007

(54) APPARATUS AND METHOD FOR TRANSVERSE CHARACTERIZATION OF MATERIALS

(75) Inventor: Patricia A. Beck, Palo Alto, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 0 days.

(21) Appl. No.: 10/835,943

(22) Filed: Apr. 29, 2004

(65) Prior Publication Data

US 2005/0242339 A1 Nov. 3, 2005

(51) Int. Cl.
*H01L 23/482* (2006.01)
(52) U.S. Cl. .............. 257/414; 257/4; 257/5; 257/E23.015; 257/E23.02; 977/836
(58) Field of Classification Search ........... 257/700, 257/701–703, 4, 5, 414, E23.015, E23.02; 438/900; 977/836
See application file for complete search history.

(56) References Cited

U.S. PATENT DOCUMENTS

| | | |
|---|---|---|
| 5,491,338 A | 2/1996 | Spitzer et al. |
| 6,476,333 B1* | 11/2002 | Khandros et al. ........... 174/267 |
| 6,756,253 B1* | 6/2004 | Farnworth et al. .......... 438/125 |
| 2004/0262636 A1* | 12/2004 | Yang et al. ................. 257/200 |
| 2005/0218464 A1* | 10/2005 | Holm-Kennedy ........... 257/414 |
| 2006/0081950 A1* | 4/2006 | Kuhr et al. ................. 257/414 |

OTHER PUBLICATIONS

Patent Abstracts of Japan—"Thin-Film resistor and its Manufacture"—vol. 018 No. 414 (E-1587) Aug. 3, 1994.

* cited by examiner

Primary Examiner—Evan Pert
Assistant Examiner—Victor A. Mandala, Jr.

(57) ABSTRACT

An apparatus for transverse characterization of materials includes a lower pattern of contacts, separated by spacings, a material, and an upper pattern of a multiplicity of contacts, separated by spacings differing from the spacings of the lower pattern. The transverse characterization method includes receiving lower pattern of a multiplicity of contacts, separated by spacings along a surface, with a material above the surface, successively placing an upper contact near the upper surface of the material in an upper pattern of locations separated by spacings differing from the spacings of the lower pattern, measuring the characteristics between the upper contact and one or more contacts of the lower pattern and evaluating the measured characteristics to previous measurements, wherein the evaluation provides the transverse characterization.

12 Claims, 5 Drawing Sheets

APPARATUS AND METHOD FOR TRANSVERSE CHARACTERIZATION OF MATERIALS

BACKGROUND

The present application is generally directed to nanoscale computing and memory circuits and, more particularly, to the characterization of the molecular films employed in such devices. The devices may have more than one stable state (e.g., bi-stable switches) and may be homogeneous or heterogeneous in nature (e.g., may be composed of one or more molecules which are uniformly or nonuniformly distributed throughout). The term "nanoscale" is used to indicate that either the horizontal or vertical dimensions or the electrical pathway between contacts is measured in nanometers.

As feature sizes of integrated-circuit devices continue to decrease, it becomes increasingly difficult to design well-behaved devices. Their fabrication is also becoming increasingly difficult and expensive. Moreover, the number of electrons either accessed or utilized within a device is decreasing, producing increased statistical fluctuations in the electrical properties. In the limit, device operation depends on a single electron, and traditional device concepts must change.

Developments in nanotechnology are directed to solving these problems using new generations of electronic circuitry, having much smaller dimensions than present technology can provide. An advantage of molecular electronic devices is that the device performance characteristics originate from molecular properties. This has several notable implications. First, it means that the devices can potentially scale down in size to nanometer dimensions without significant change(s) in device performance. Second, it also means that the unique electronic properties designed into these molecular structures can be aggregated and designed into solid state devices.

Molecular electronics has the potential to augment or even replace conventional devices with electronic elements, can be altered by externally applied voltages or fields, and has the potential to scale from micron-scale dimension to nanometer-scale dimensions with little change in the device concept. Examples of such molecular electronic devices include, but are not limited to, crossed wires, nanoporous surfaces, and tip addressable circuitry which forms switches, diodes, resistors, transducers and other active components.

For instance, a crossed-wire switch may comprise two wires, or two contacts, for example, with a molecular switching species between the two contacts. Thin single or multiple molecular layers can be formed, for example, by Langmuir-Blodgett (LB) techniques or by a self-assembled monolayer (SAM) on a specific site. The self-assembled switching elements may be integrated on top of a semiconductor integrated circuit so that they can be driven by conventional semiconductor electronics in the underlying substrate. To address the switching elements, interconnections, probes or wires are used. (The term "self-assembled" as used herein refers to a system that naturally adopts some regular pattern because of the identity of the components of the system; the system achieves at least a local minimum in its energy by adopting this configuration.)

Despite its great promise, the area of molecular electronics is still in its infancy. An early step towards molecular computing was to produce a bistable molecular device capable of encoding a logical 1 or 0 such as when switched from a "high" or "on" state to a "low or off" state. For nanoscale electronic circuits, new materials may be invented with the functions envisioned for them and new processes to fabricate them. Nanoscale molecules with special functions can be potentially used as basic elements for nanoscale computing and memory applications.

For example, a bi-stable molecule, such as rotaxane, pseudo-rotaxane, or catenane, formed between contacts could create a switch at the molecular level. An array of such switches could form logical circuits or memory structures. Application of a voltage across a selected pair of contacts connected by the molecular species of interest would cause the change in state. The term "bi-stable" as applied to a molecule refers herein to a molecule having two relatively low energy states. The molecule may be either irreversibly switched from one state to another (singly configurable) or reversibly switched from one state to another (reconfigurable).

Characterization of both molecular films and the molecules comprising such films generally occurs on a substrate, not in solution, with contacts formed using conventional semiconductor processing techniques. Characterization of such devices has typically been via two contacts normal to the surface of an assembled or transferred film, where the film is akin to a page or set of pages and the contacts are opposing covers of a closed book. This characterization may employ contacts of micron or nanometer scale.

Unfortunately, this method does not allow access to properties at other angles, due to the small thickness of the film and discretely contacting the longitudinal edges of the film (as in the spine of the book) is extremely difficult due to the small thickness of the film. There is a present and future need for a practical technique to perform such non-normal angle characterization and fully investigate sample properties in multiple directions.

BRIEF DESCRIPTION OF THE DRAWINGS

The present invention is illustrated by way of example and not limitation in the figures of the accompanying drawings in which.

SUMMARY OF THE INVENTION

Figure 1A:
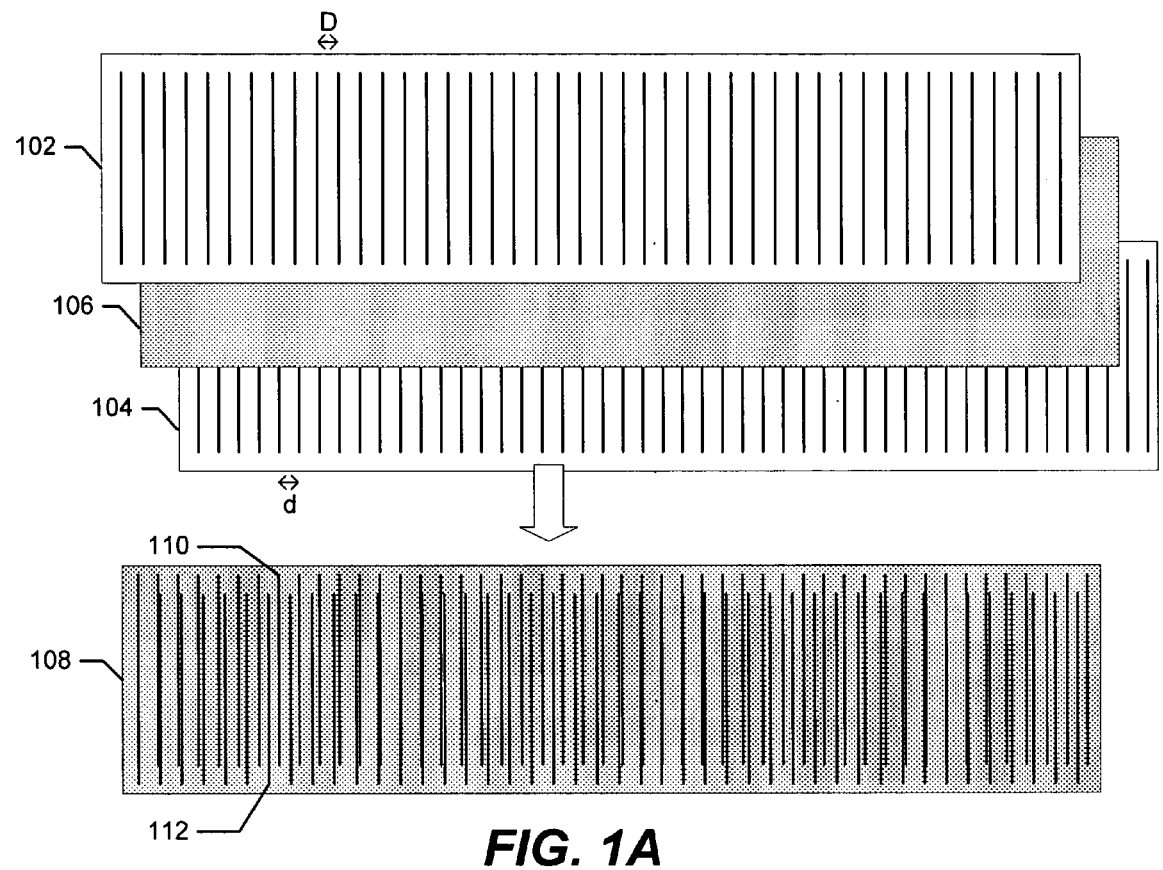
FIG. 1A is a schematic diagram showing the arrangement of the three main layers of an embodiment for measuring characteristics of a material, viewed from a direction perpendicular to the layers.

One aspect of the present invention features an apparatus for transverse characterization of materials, comprising a lower pattern of contacts, separated by spacings; a material above the surface of the lower pattern; and an upper pattern of contacts, separated by spacings differing from the spacings of the lower pattern, above the upper surface of the material.

Another aspect of the present invention features a method for transverse characterization of materials, comprising: arranging a lower pattern of contacts, separated by spacings, beneath the lower surface of a material; arranging an upper pattern of contacts, separated by spacings differing from those of the lower pattern, above the upper surface of the material, measuring the characteristics between two or more of the contacts; and evaluating the successively measured characteristics with respect to angle, distance and other geometric conditions.

The details of one or more embodiments of the invention are set forth in the accompanying drawings and the description below. Other features and advantages of the invention will become apparent from the description, the drawings, and the claims.

DETAILED DESCRIPTION

The present application is related to U.S. Pat. No. 6,459,095, issued Oct. 1, 2002, by James R. Heath, R. Stanley Williams, and Philip J. Kuekes, entitled "Chemically Synthesized and Assembled Electronic Devices"; U.S. Pat. No. 6,314,019, issued Nov. 6, 2001, by James R. Heath, R. Stanley Williams, and Philip J. Kuekes, entitled "Molecular Wire Crossbar Interconnect (MWCI) for Signal Routing and Communications"; U.S. Pat. No. 6,128,214, issued on Oct. 3, 2000, by James R. Heath, R. Stanley Williams, and Philip J. Kuekes, entitled "Molecular Wire Crossbar Memory"; U.S. Pat. No. 6,458,621, issued on Oct. 1, 2002, by Patricia A. Beck, entitled "Batch Fabricated Molecular Electronic Devices with Cost Effective Lithographic Electrodes"; U.S. Pat. No. 6,579,742, by Yong Chen, entitled "Fabrication of Molecular Electronic Circuit by Imprinting"; and U.S. Pat. No. 6,559,468, issued on May 6, 2003, by James R. Heath, R. Stanley Williams, and Philip J. Kuekes, entitled "Molecular Wire Transistor (MWT)." Each of the foregoing is assigned to the assignee of the present invention and is incorporated herein by reference.

In accordance with the present invention, an apparatus and method are provided for transverse characterization of materials. The method is suitable for characterizing many materials, including without limitation films of which the various electronic structures have micron to submicron to nanometer scale dimensions. Micron-scale dimensions refers roughly to dimensions that range from 1 micrometer to a few micrometers in size while sub-micron scale dimensions refers roughly to dimensions that range from 1 micrometer down to 0.05 micrometers and nanometer scale dimensions refers roughly to dimensions that range from 1 nanometers up to 50 nanometers (0.05 micrometers).

Molecular electronics technology aspires to use a small number or even a single molecule to perform the functions of electronic devices. Many functions performed by conventional electronic devices can potentially be synthesized at the molecular level. For example, different combination of molecules might be formed into molecular layers exhibiting charge storage (capacitor), signal rectification (diodes), signal dissipation (resistors) or signal inversion (negative differential resistance) at other non-normal-angle molecular arrangements. Together, these devices might perform various tasks, such as logical operations, memory storage, or signal routing.

FIG. 1A is a schematic diagram showing the arrangement of the three main layers of an embodiment for measuring properties of a material, viewed from a direction perpendicular to the layers. These layers include an upper pattern of contacts 102, a lower pattern of contacts 104, and a material 106. As will be described in further detail, both layout and positioning of the upper pattern of contacts 102 and lower pattern of contacts 104 facilitate making transverse measurements through the material 106.

In the embodiment shown, contacts in the upper pattern 102 are separated by a spacing distance D while the contacts of the lower pattern 104 are separated by a different spacing distance d. The distances D and d are measured in this example from the center of one electrode to the center of the next, as is the convention. The ratio of the spacing distance D of the upper pattern and the spacing distance d of the lower pattern is equal to the fraction D/d—referred to hereinafter as the "vernier ratio" of these patterns. If the vernier ratio is also equal to the fraction A/B, where A and B are integers, then the pattern will repeat. When these layers are combined in a single structure 108, the two patterns of contacts combine to form a visible vernier pattern. In this context, "vernier pattern" refers to the pattern formed by two sets of lines or marks with differing spacings, superimposed or placed near each other along a single dimension or surface. It becomes easier, in such a pattern, to identify regions where the marks are exactly in phase or out of phase. This in turn aids measurement and experimentation.

Note that FIG. 1A is schematic in nature not drawn to any scale, and that in practice it is often desirable for the contacts to be much shorter in length than the spacing between them. This reduces such problems as cross-talk or inductance among the contacts when they are energized. The contacts are not necessarily rectangular or substantially longer in one dimension than another, and may be made different shapes or sizes, depending on the method of manufacture and desired effect.

Making use of the device, an experimenter may, for instance, apply a voltage difference to two contacts 110 and 112 on opposite sides of the material, and may ground the rest of the contacts. The contacts selected to receive the voltage are offset by a known amount according to the previously described vernier ratio. Accordingly, the transverse angle for characterizing the properties of the material is determined by selecting different pairs of contacts in the desired area of the vernier pattern and according to the vernier ratio. Depending on the actual dimensions, the different transverse angles available for measuring the material or molecules in a film vary according to the visible offset pattern between contacts in upper pattern 102 and lower pattern 104 as combined together into single structure 108.

One application of this arrangement is to examine the properties of bi-stable switching molecules, or other molecules with some desirable electronic characteristic or even filament growth, grain boundaries, rotation in a certain direction, etc. In the example illustrated in FIG. 1A, molecules are deposited onto the substrate surface forming thin material 106 from a molecular layer and covering the substrate surface formed by lower pattern 104 and upper pattern 102. The molecular film may be deposited as a Langmuir film or Langmuir-Blodgett multilayer thin film. In alternative implementations, the molecules may also be deposited via a chemical reaction that bonds portions of the molecule with the contacts, on a transfer layer over the contacts, and/or using a magnetic field or other force to ensure proper orientation of the molecules in the film. The techniques used in creation and manipulation of thin films are rapidly evolving, and application of the present invention is not limited to any particular technique.

Contact patterns created in accordance with the present invention can be formed using many different types of patterning techniques, such as those known in the semiconductor industry and nano-technology community. Photolithography using radiation (usually UV, ebeam or X-ray), focused ion beam, and nano-imprinting are all examples. In general, the resolution of the resulting contact patterns should only be limited by the particular lithographic or other patterning approach used. For example, contact patterns formed using optical, electron or ion beam lithography would have the resolution of the respective underlying patterning technology.

Figure 1B:
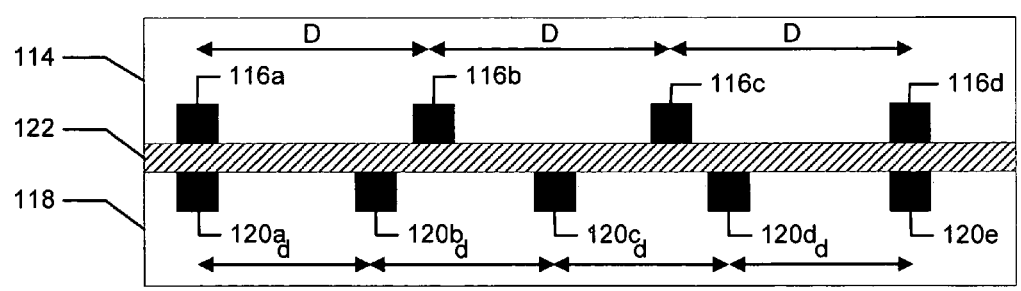
FIG. 1B is a cross-section schematic diagram illustrating a structure designed in accordance with another embodiment of the present invention.

FIG. 1B is a cross-section schematic diagram illustrating a structure designed in accordance with another implementation of the present invention. This structure includes an upper substrate 114 containing a pattern of contacts 116a–d and a lower substrate 118 containing a pattern of contacts 120a–e near a material 122 having an upper surface and a lower surface. As previously described, the vernier ratio describes the contact geometry and is a ratio of the spacing distance D of the upper pattern and the spacing distance of the lower pattern. If the vernier ratio is also equal to the fraction A/B, where A and B are integers, then the pattern will be repeating. In this example, this results in contact 116a substantially coincident with contact 120a and contact 116d substantially coincident with contact 120e. In between pairs of contacts 116a/120a and contacts 116d/120e, other contact pairs transition from the coincident positions to positions described by various predetermined offsets. The pairs may be at an angle between zero and 90 degrees. In other words, a line drawn between two selected contacts can be at an angle from a line normal to surface of the material. This allows the experimenter to control the angle of measurement through the material. These latter positions are used to make transverse measurements of the material, or if the material is a film, the molecules in it.

FIG. 1B is, again, schematic in nature. The material 122 in the diagram appears to lie exactly along a plane, but in practice this is difficult to accomplish, especially if the material is a film. Depending on the particular manufacturing process used, there may be depressions between the contacts, and the material may lie lower in these depressions. This may or may not be a desirable property, depending on the particular characteristics that are sought to be characterized. It is also possible to planarize the surface using various techniques known in the semiconductor industry, such as chem-mechanical polishing techniques, a Damascene process or by the use of other etch-back techniques.

Figure 2A:
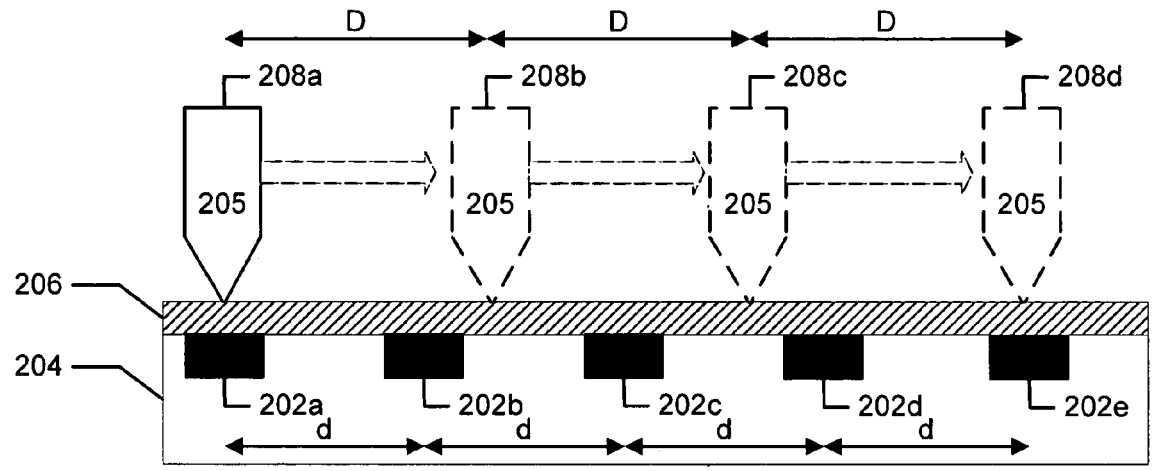
FIG. 2A is a schematic diagram showing a cross-section of another embodiment making a virtual vernier pattern with a microcantilever such as one used in an atomic force microscope.

FIG. 2A is a schematic diagram showing a cross-section of another embodiment making a virtual vernier pattern with a moveable second contact such as a microcantilever found in an atomic force microscope, or as is sometimes used in "tip addressable" circuitry. An atomic force microscope operates by scanning a probe tip over a surface and monitoring the position in response to changes in surface topography. The tip is fabricated so that its extreme edge is on the scale of a single atom or molecule. In this implementation, a pattern of contacts 202a–e is arranged in a substrate 204 and beneath a material 206. A probe tip 205 of the microscope 208a is moved to subsequent positions 208b, 208c and 208d and remains either in contact with or proximity to material 206. At the first location 208a, probe tip 205 coincides with contact 202a and measures characteristics of the material normal to its surface. At subsequent positions 208b and 208c, probe tip 205 measures characteristics of the material at non-normal angles (drawn connecting the contacts) to contact 202a, 202b, 202c, 202d, or 202e. Eventually, probe tip 205 arrives at a location 208d where it again coincides with a contact beneath material 206.

Figure 2B:
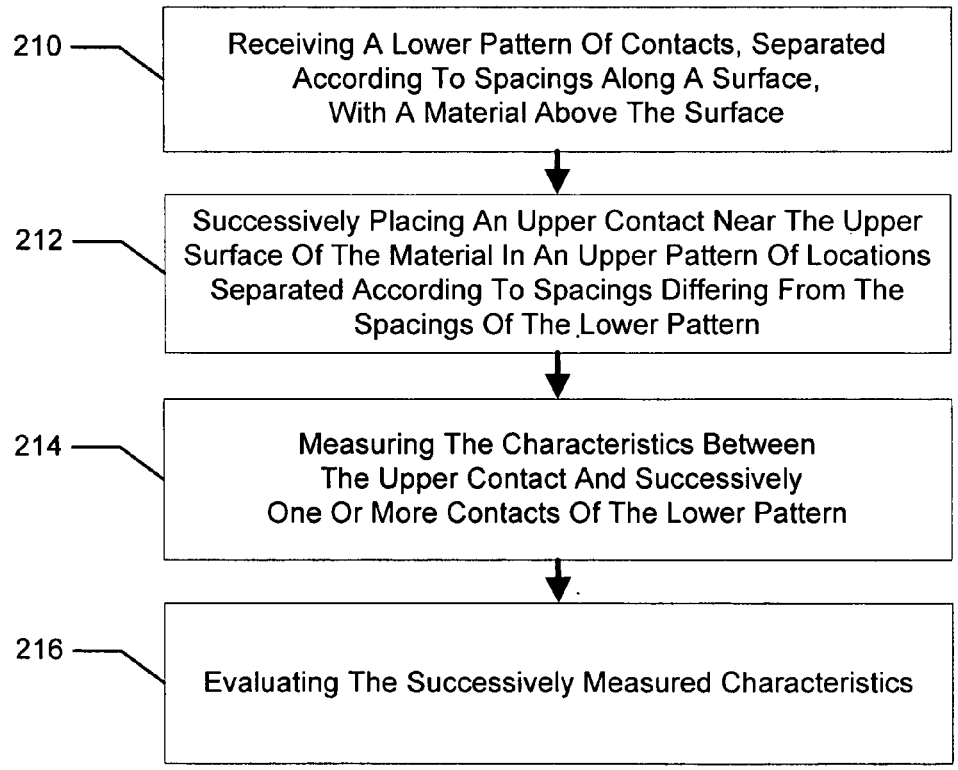
FIG. 2B is a flowchart showing a method for characterizing the transverse characteristics of materials using the apparatus of FIG. 2A.

FIG. 2B is a flowchart showing one method of transversely characterizing materials using a virtual vernier pattern generated in accordance with the present invention. Initially, the characterization operation includes receiving a multiplicity of contacts arranged according to a lower pattern of spacings with a material above the surface (210). For example, contacts in FIG. 2A are separated by a predetermined spacing distance d.

The virtual vernier pattern is generated by successively positioning a contact on the upper surface of the material according to an upper pattern of locations separated by a gap differing from the location of spacings of the lower pattern (212). In one implementation, the atomic force microscope previously described in FIG. 2A creates the contact using probe tip 205. Rather than using gap d, the upper pattern is formed moving probe tip 205 along spacings of size D creating the virtual vernier ratio D/d. The successive positioning of the contact need not follow the order from left to right or right to left—positions can be measured in any order.

Once positioned, measurements of the characteristics of the material are made transversely in accordance with the upper and lower patterns (214). The upper and lower patterns describe a transverse path through the material due to their difference in alignment. Different potential characteristics of the material can be explored along this transverse path dynamically as the atomic force microscope traces along the upper pattern, for instance by applying a voltage or current through the cantilever of the microscope. Because the alignment differences are predetermined, a set of transverse characterization measurements can be evaluated and compared (216) for incremental changes or new characteristics associated with the material under study.

Figure 3:
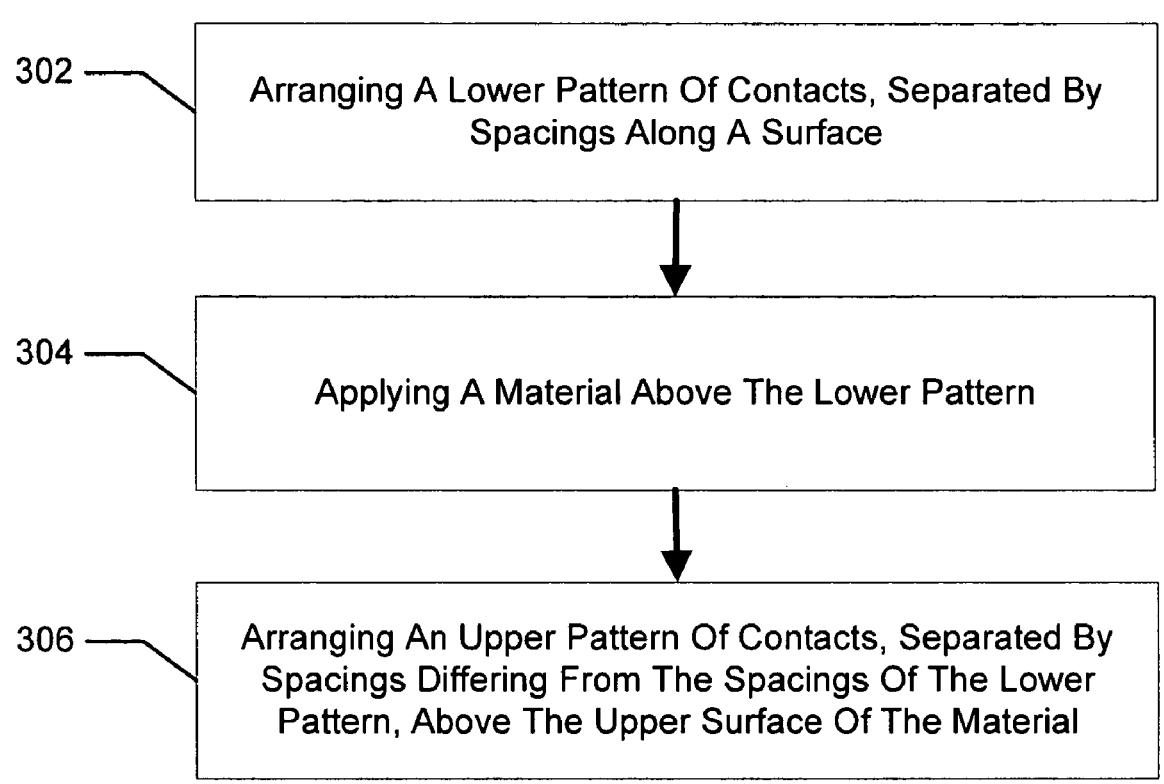
FIG. 3 is a flowchart showing a method of manufacture of an embodiment of the invention.

FIG. 3 is a flowchart showing a method of manufacture of an embodiment of the invention such as that illustrated in FIG. 1. The manufacturer first arranges a lower pattern of a multiplicity of contacts, separated by spacings along a surface (302).

The manufacturer then applies a material above the lower pattern (304). The material may be, but is not necessarily, a film. If a film, it may be a single or multi-molecule thin film. In the case of thin films, the molecular film can be deposited as a Langmuir film or Langmuir-Blodgett multilayer thin film. In alternative implementations, the molecules may also be deposited via a chemical reaction that bonds portions of the molecule with the contacts, on a transfer layer over the contacts, and/or using a magnetic field or other force to ensure proper orientation of the molecules in the material. Moreover, the structures described may themselves comprise additional layers or structures. For example, the contacts may include an oxidized layer, which has been found by experiment to be useful in some circumstances. The techniques used in creation and manipulation of thin films are rapidly evolving, and application of the present invention is not limited to any particular technique.

The manufacturer then arranges an upper pattern of a multiplicity of contacts, separated by spacings differing from the spacings of the lower pattern, above the upper surface of the material (306). In one possible embodiment, the two patterns have constant spacing distances D and d, where D/d is equal to the ratio of two integers A and B; this creates the vernier pattern.

Figure 4:
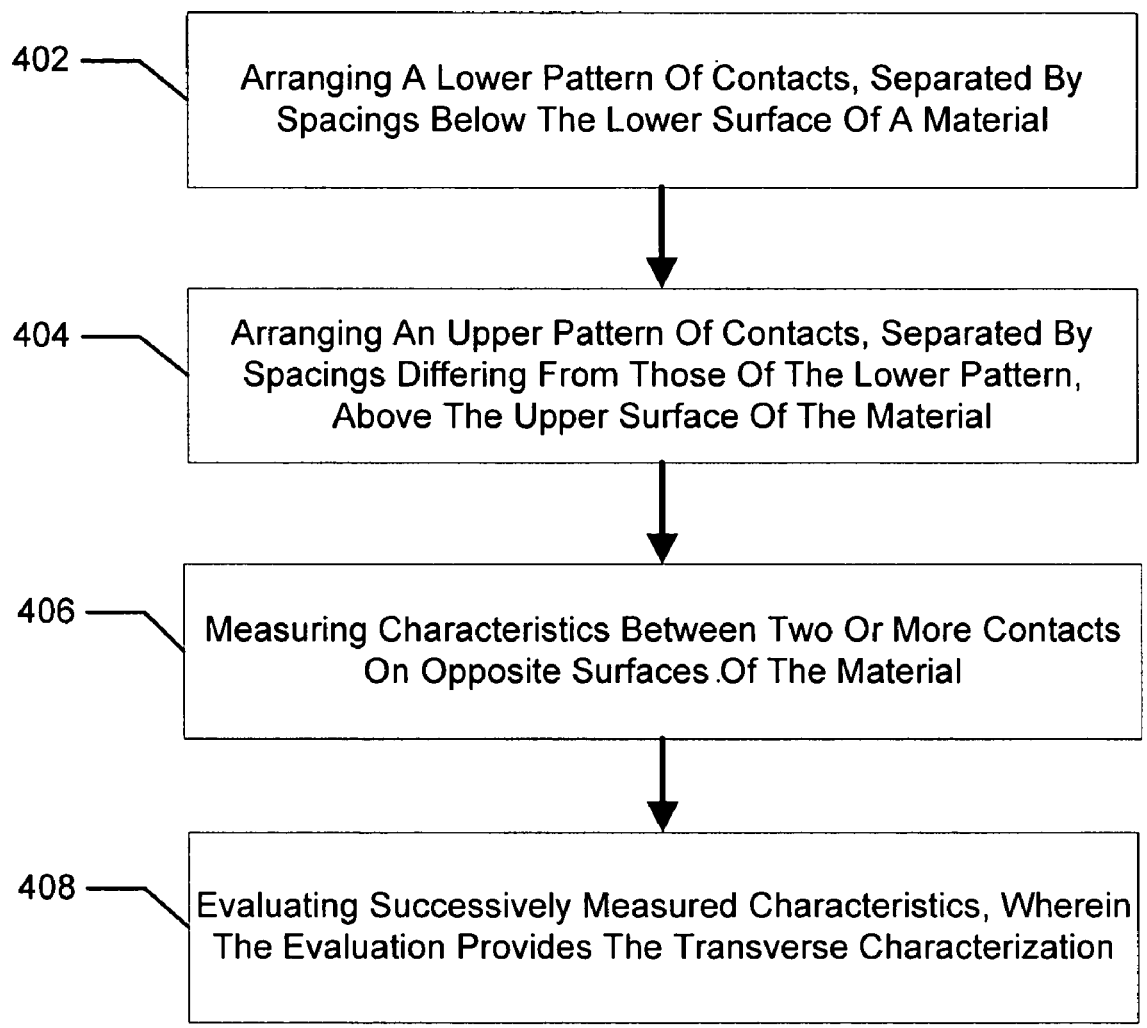
FIG. 4 is a flowchart showing a method for measuring the transverse characteristics of a material using an embodiment of the invention.

FIG. 4 is a flowchart showing a method for measuring the transverse characteristics of a material using fixed conducts in another embodiment of the invention. Unlike the virtual vernier pattern described previously, this operation uses a fixed vernier pattern set by multiple contacts arranged in an offset position. In this case, the experimenter arranges a lower pattern of contacts, separated by spacings beneath the lower surface of a material (402).

The experimenter then arranges an upper pattern of a multiplicity of contacts, separated by spacings differing from those of the lower pattern, above the upper surface of the material (404). As described before, one possible embodiment includes the creation of a visible vernier pattern between the two sets of contacts. In order to create a vernier pattern, the ratio of the spacing distance D of the upper pattern and the spacing distance d of the lower pattern can be set to the fraction A/B, where A and B are integers.

The experimenter then measures characteristics between contacts of choice on opposite surfaces of the material (406) to measure the properties of the material at a desired angle. The experimenter may, for instance, activate two or more such contacts to measure at particular angles through the material, and may ground surrounding contacts. The experimenter can successively select various groups of contacts and evaluate the measured characteristics (408). The successive selection need not follow any particular order—single or multiple contacts above and below the material can be selected at will by the experimenter. One product of prior measurement techniques has been the growth of filaments between contacts in particular devices. By allowing at-will characterization at different angles and locations of the material, the current technique enables the experimenter to isolate and identify such phenomena.

Referring again to FIG. 1A, it is apparent that the material may be affected or measured at various angles, depending on the arrangement of contacts. In the configuration shown, an experimental measurement may be performed in a line normal (an angle of zero degrees) to the surface (116$a$ and 120$a$), at a slight angle to the surface (116$b$ and 120$b$, or 116$c$ and 120$d$), or at a greater angle approaching 90 degrees from vertical (116$a$ and 120$c$). For some embodiments and contact gap scales, an experimenter can conveniently calibrate the angle of measurement by optically observing the vernier pattern at different regions of the material (see FIG. 1A) alleviating the need for precise alignment of an upper and lower contact set.

Figure 5:
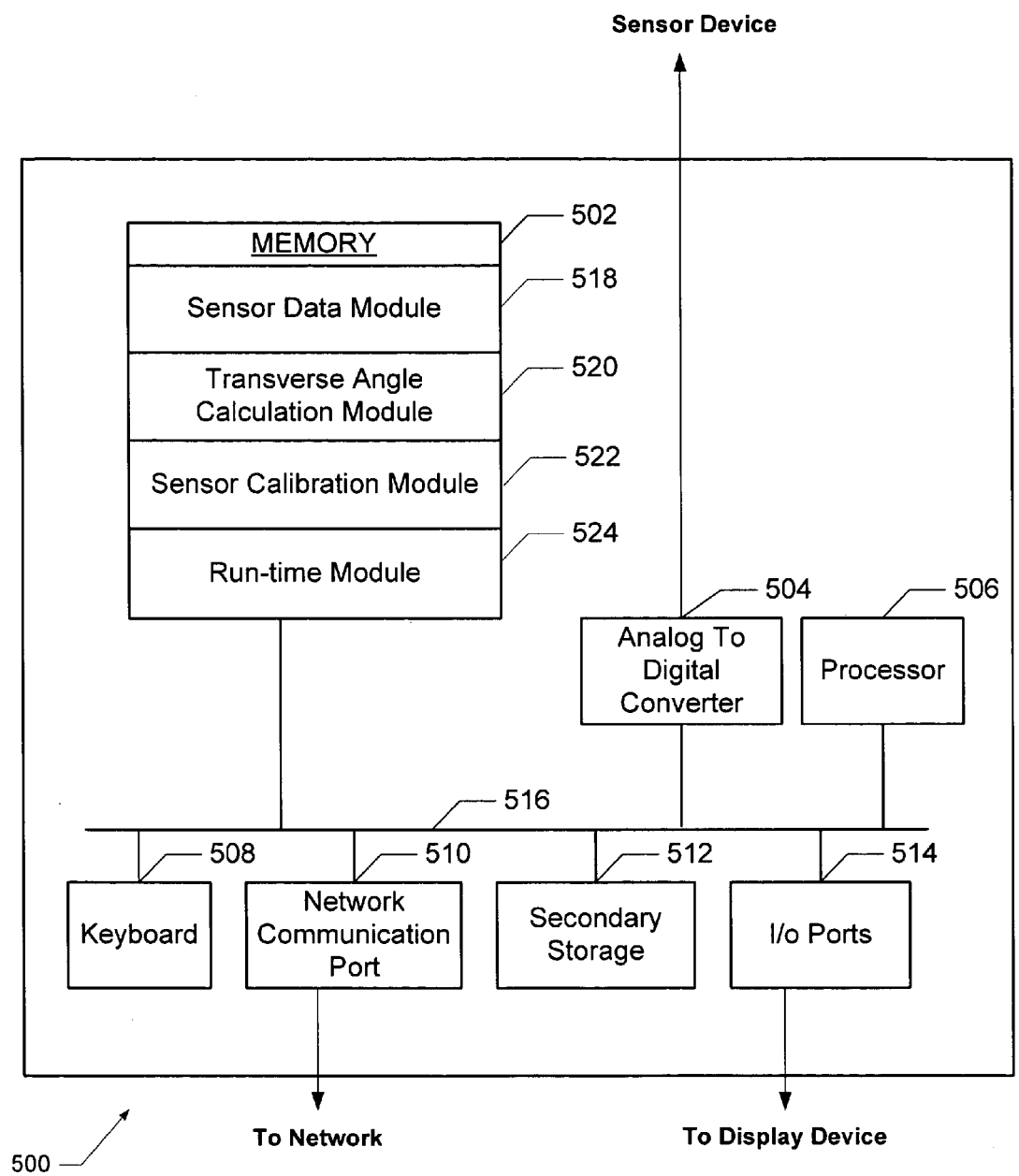
FIG. 5 is a schematic showing the software and hardware components in a device used to control an embodiment of the invention.

FIG. 5 is a block diagram of a system 500 used in one implementation. System 500 includes a memory 502 to hold executing programs (typically random access memory (RAM) or read-only memory (ROM) such as a flash ROM), an Analog to Digital Converter 504 capable of interfacing with a measurement device, a processor 506, a program memory 502 for holding drivers or other frequently used programs, a keyboard 508, a network communication port 510 for data communication, a secondary storage 512 with a secondary storage controller and input/output (I/O) ports and controller 514 operatively coupled together over an interconnect 516. System 500 can be preprogrammed, in ROM, for example, using field-programmable gate array (FPGA) technology or it can be programmed (and reprogrammed) by loading a program from another source (for example, from a floppy disk, a CD-ROM, or another computer). Also, system 500 can be implemented using customized application specific integrated circuits (ASICs).

In one implementation, memory 502 includes a Sensor Data Module 518, a Transverse Angle Calculation Module 520, a Sensor Calibration Module 522, and a run-time module 524 that manages system resources used when processing one or more of the above components on system 500.

Having thus described exemplary embodiments of the present invention, it should be noted by those skilled in the art that the within disclosures are exemplary only and that various other alternatives, adaptations and modifications may be made within the scope of the present invention. For example, a variety of lithographic techniques or equivalents is available or will become available and could be used to embody the described invention. The contacts and material may be composed of a variety of substances and configurations. Contacts may be used to measure capacitance, resistance, inductance, or other properties of molecules. Various arrangements and patterns of contacts are possible. The technique can measure the characteristics of multi-layer films or layers, gases, liquids, solids, or many other forms of matter. The technique can also measure the characteristics of the contacts themselves, where the "material" that exists between the two patterns of contacts is either matter or one or more fields or other physical properties. Moreover, "user," "manufacturer," "experimenter," and other terms have been used to describe an individual using or practicing the methods and systems described here, but no limitation is implied by that; and the methods and systems described here may be used for experiment or in practical applications. Accordingly, the invention is not limited to the above-described implementations, but instead is defined by the appended claims in light of their full scope of equivalents.

What is claimed is:

1. An apparatus for transverse characterization of a material, comprising:
   a lower pattern of a multiplicity of contacts, separated according to spacings along a surface;
   a material having at least one dimension on a micron, submicron or nanometer scale above the lower pattern of contacts; and
   an upper pattern of a multiplicity of contacts, separated according to spacings differing from the spacings of the lower pattern, above the upper surface of the material to allow a transverse characterization of the material above the lower pattern of contacts.

2. The apparatus of claim 1, wherein one or both patterns of contacts is formed on a substrate selected from a set of substrates including: silicon, polyimide, alumina, mica, quartz, sapphire, SiC, DLC (diamond-like carbon), FeAlN, and FeTaN.

3. The apparatus of claim 1, wherein at least one pattern of contacts is formed by a technique selected from a set of techniques including: UV lithography, X-ray lithography, electron beam lithography, ion-milling, laser ablation, focused ion beam patterning, laser-assisted deposition, electron-assisted deposition, photo-assisted deposition, AFM/STM-assisted deposition, imprinting, nano-imprinting, and electroplating, employing either lift-off or etching.

4. The apparatus of claim 1, wherein the contacts of the lower pattern are different in width than the contacts of the upper pattern along at least one dimension of contact.

5. The apparatus of claim 1, wherein the material is selected from a set of materials including: liquids, gases, solids and plasmas.

6. The apparatus of claim 1, wherein the material is a molecular film.

7. The apparatus of claim 6, wherein the film is formed and received using a Langmuir-Blodgett technique.

8. The apparatus of claim 6, wherein the film comprises molecules having bi-stable properties.

9. The apparatus of claim 1, wherein the lower contacts are separated by a first constant spacing distance, and the contacts of the upper pattern by a second constant spacing distance.

10. The apparatus of claim 9, wherein the ratio of the spacing distance D of the upper pattern and the spacing distance d of the lower pattern is equal to the fraction A/B, where A and B are integers.

11. The apparatus of claim 10, wherein the lower and upper patterns of contacts are overlaid to form a vernier pattern.

12. An apparatus for transverse characterization of a material, said apparatus, comprising:

means for arranging a lower pattern of a multiplicity of contacts, separated by spacings along the lower surface of a material having at least one dimension on a micron, submicron or nanometer scale;

means for arranging an upper pattern of a multiplicity of contacts, separated by spacings differing from those of the lower pattern, along the upper surface of the material;

means for measuring characteristics between two or more contacts on opposite sides of the material to allow a transverse characterization of the material; and means for evaluating successively measured characteristics, wherein the evaluation provides the transverse characterization.

* * * * *